United States Patent
Che

(10) Patent No.: US 11,958,977 B2
(45) Date of Patent: Apr. 16, 2024

(54) FLUORESCENTLY LABELED POLYSACCHARIDE, PREPARATION METHOD THEREFOR, AND USE THEREOF

(71) Applicant: SUZHOU BAIYUAN GENT CO., LTD., Jiangsu (CN)

(72) Inventor: Tuanjie Che, Jiangsu (CN)

(73) Assignee: SUZHOU BAIYUAN GENT CO., LTD., Jiangsu (CN)

( * ) Notice: Subject to any disclaimer, the term of this patent is extended or adjusted under 35 U.S.C. 154(b) by 697 days.

(21) Appl. No.: 17/056,501

(22) PCT Filed: Jun. 12, 2018

(86) PCT No.: PCT/CN2018/090781
§ 371 (c)(1),
(2) Date: Nov. 18, 2020

(87) PCT Pub. No.: WO2019/227528
PCT Pub. Date: Dec. 5, 2019

(65) Prior Publication Data
US 2021/0214559 A1    Jul. 15, 2021

(30) Foreign Application Priority Data
May 29, 2018 (CN) .......................... 201810535573.2

(51) Int. Cl.
| C09B 23/08 | (2006.01) |
| C08B 37/08 | (2006.01) |
| C09B 23/01 | (2006.01) |
| C09K 11/06 | (2006.01) |
| G01N 33/58 | (2006.01) |

(52) U.S. Cl.
CPC .......... *C09B 23/086* (2013.01); *C08B 37/003* (2013.01); *C09B 23/0041* (2013.01); *C09B 23/0066* (2013.01); *C09K 11/06* (2013.01); *G01N 33/582* (2013.01); *C09K 2211/1029* (2013.01); *G01N 2400/10* (2013.01)

(58) Field of Classification Search
CPC ............ C09K 11/06; C09K 2211/1029; C08B 37/003; C08B 23/0041; C08B 23/0066; G01N 33/582; G01N 2400/10
See application file for complete search history.

(56) References Cited

U.S. PATENT DOCUMENTS

2011/0117666 A1    5/2011  Nagano et al.
2021/0206979 A1*   7/2021  Che .................... C09B 23/0066

FOREIGN PATENT DOCUMENTS

| CN | 1702118 A | 11/2005 |
| CN | 103242822 A | 8/2013 |
| CN | 104893710 A | 9/2015 |
| JP | 6236469 A | 2/1987 |
| JP | 5559529 B2 | 6/2014 |
| JP | 2017031394 A | 2/2017 |
| WO | 2010083471 A1 | 7/2010 |
| WO | 2012048063 A2 | 4/2012 |

OTHER PUBLICATIONS

International Search Report dated Mar. 6, 2019 based on International Application No. PCT/CN2018/090781.
Written Opinion of the International Searching Authority dated Mar. 6, 2019 based on International Application No. PCT/CN2018/090781.
Notification of First Office Action in related Chinese Application No. 201810535573.2 dated May 10, 2019.
Notification of Second Office Action in related Chinese Application No. 201810535573.2 dated Jan. 20, 2020.
Notification of Third Office Action in related Chinese Application No. 201810535573.2 dated Apr. 3, 2020.
First Office Action issued in corresponding Japanese Patent Application No. 2019-526322, dated Nov. 4, 2021 (English translation).
First Office Action mailed Feb. 15, 2024 in corresponding Korean Patent Application No. 10-2020-7033256.

* cited by examiner

*Primary Examiner* — C Melissa Koslow
(74) *Attorney, Agent, or Firm* — Miles & Stockbridge PC; Ajay A. Jagtiani

(57) ABSTRACT

Disclosed is a fluorescently labeled polysaccharide. The fluorescently labeled polysaccharide is formed by covalently coupling a polysaccharide to a fluorescent dye having a structure as shown in Formula I. A stable covalent bond is form between the polysaccharide molecule and the fluorescent dye molecule. The fluorescently labeled polysaccharide has high stability in serum and other detection environments, has high biocompatibility, and is applicable to the detection of carbohydrate molecules inside and outside cells. Due to a large Stokes shift of the fluorescent dye molecule, the fluorescently labeled polysaccharide has advantages of high fluorescence stability, high fluorescence quantum yields, and achieves high signal-to-noise ratios in imaging results. Further disclosed is a method for preparing the fluorescently labeled polysaccharide. The method has mild reaction conditions and high reaction selectivity, is simple to execute, and can be used to prepare a fluorescently labeled polysaccharide in high yield.

17 Claims, 3 Drawing Sheets

FLUORESCENTLY LABELED POLYSACCHARIDE, PREPARATION METHOD THEREFOR, AND USE THEREOF

CROSS-REFERENCE TO RELATED APPLICATIONS

This application is a National Stage of International Application No. PCT/CN2018/090871 filed on Jun. 12, 2018, which is hereby incorporated by reference in its entirety.

TECHNICAL FIELD

The present application relates to a field of medical biological detection, in particular to a fluorescently labeled polysaccharide, preparation method therefor, and use thereof.

BACKGROUND

A fluorescently labeled technology refers to a technology for labeling a substance capable of emitting fluorescence by a covalent bond or physical adsorption on a certain group of the studied molecule, using its fluorescence characteristics to reflect the information of the studied subject. The fluorescently labeled reagent adsorbs or covalently binds to the studied subject such as polysaccharide, nucleic acid, protein and polypeptide, thus its fluorescence characteristics are changed, reflecting the information of the performance of the studied subject. With continuous developments of modern medicine and biological technology, discovery of new fluorescently labeled dyes and use of various advanced fluorescence detection technologies and instruments, such as flow cytometer (FCM), laser scanning confocal microscopy (LSCM), the fluorescently labeled technology, as a non-radioactive labeling technology, has the characteristics of simple operation, high stability, high sensitivity and good selectivity, and may be widely used in intracellular and extracellular substance detection, tissues' and live animal's marker imaging, drug analysis, pathological model research and early diagnosis of diseases, etc., playing an important role in the field of biomedical research.

A polysaccharide is a sugar chain formed by dehydration polymerization of a plurality of monosaccharide molecules and linking by glycosidic bonds. The polysaccharide is an important biopolymer that has the function of storing energy and composing structure in living things. In recent years, with the continuous development of sugar chemistry and sugar biology, polysaccharides derived from various traditional Chinese medicines such as plants, marine organisms and fungi have emerged as an important type of biologically active natural products. It has been found from a large number of studies that polysaccharides derived from Chinese medicine participate in and mediate the regulation of various life activities in cells, and have biological activities such as antitumor activity, antibacterial activity, immune regulation activity, hypoglycemic activity, antiviral activity, antioxidation activity, hypolipidemic activity, anticoagulant activity, antihypoxia activity, antiaging activity, and has little toxic side effects on the body. Therefore, the detection of polysaccharides is of great significance for the research and development of carbohydrate-based drugs. Fluorescence detection is widely used in polysaccharide detection because of its advantages such as high sensitivity, good selectivity, wide dynamic response range, and in-vivo detection. Since the polysaccharide itself lacks luminophore and fluorophore, in the fluorescence detection of the polysaccharide, it is necessary to bind the fluorescent substance to the reducing terminus of the polysaccharide. The qualitative and quantitative study of the polysaccharide is realized by detecting the fluorescent substance.

At present, there are many commercially available fluorescent dyes, which have a widely distributed spectral range covering from blue to red, and can be directly available in the market. However, the existing fluorescent dyes also have many problems, for example, the fluorescent dyes have a Stokes shift generally not exceeding nm, are easily quenched, have unstable signals, and are difficult to achieve distinction of different fluorescent signals, which limits the fluorescence detection of sugar molecules.

SUMMARY

Therefore, the technical problem to be solved by the present application is to overcome the defects in the prior art that the fluorescently labeled polysaccharide has a small Stoke shift and an unstable fluorescence signal, and is difficult to effectively distinguish different fluorescent signals.

In order to solve the above technical problems, the present application provides a fluorescently labeled polysaccharide, wherein the fluorescently labeled polysaccharide is formed by covalently coupling a polysaccharide to a fluorescent dye having a structure represented by the formula (I):

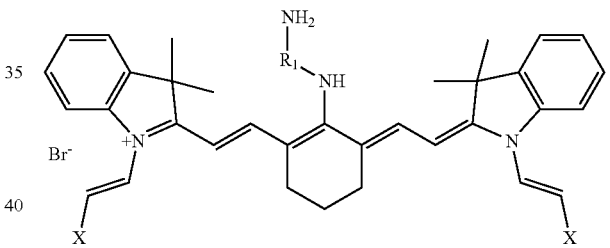

wherein X is halogen; $R_1$ is selected from one of hydrogen, [alkylene], cycloalkyl, aryl and heterocyclyl.

Optionally, in the fluorescently labeled polysaccharide, the polysaccharide is activated by cyanogen bromide, hydroxyl of the polysaccharide binds to cyano, and the cyano binds to amino of the fluorescent dye.

Optionally, in the fluorescently labeled polysaccharide, X is Br.

Optionally, in the fluorescently labeled polysaccharide, the fluorescent dye has a structure represented by formulas B to G:

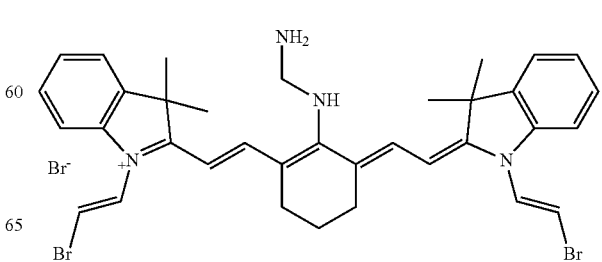

-continued

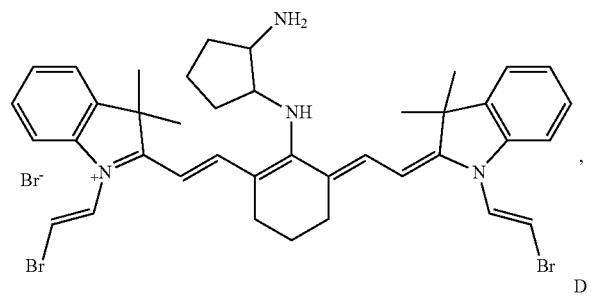
C

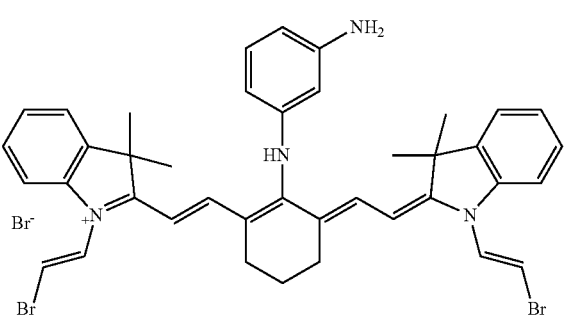
D

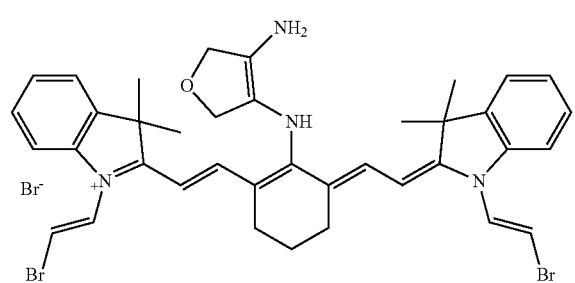
E

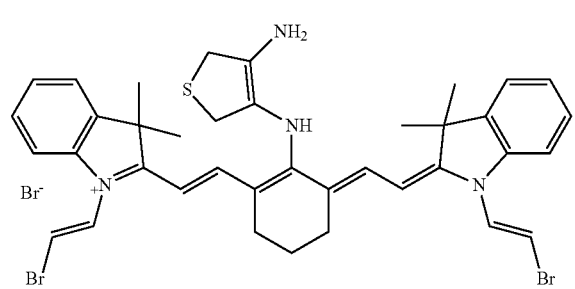
F

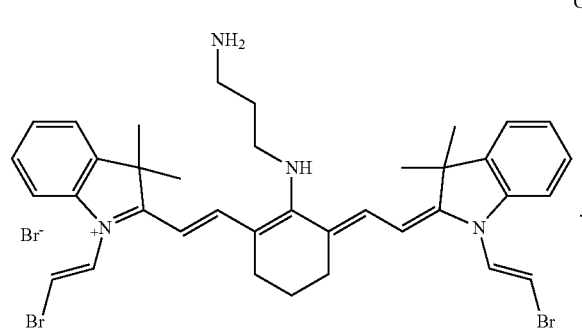
G

Optionally, in the fluorescently labeled polysaccharide, the polysaccharide is selected from at least one of glucan, chitosan, pectic polysaccharide, grifola frondosa polysaccharide, ganoderan, lentinan and spriulina polysaccharide.

The present application also provides a method of preparing the fluorescently labeled polysaccharide, comprising the steps of:

(1) dissolving the polysaccharide in water, and then adding a saturated cyanogen bromide solution for reaction for 3-20 minutes, and purifying the solution obtained after the reaction;

(2) concentrating the purified solution obtained in the step (1) to dry, dissolving in 0.1-0.3 M borax solution, and then adding a fluorescent dye represented by the formula I for reaction in the dark to obtain the fluorescently labeled polysaccharide.

Optionally, in the step (1) of the method of preparing the fluorescently labeled polysaccharide, the reaction is carried out under the condition of pH>10; and/or, the reaction time is controlled for 5-10 minutes.

Optionally, in the step (2) of the method of preparing the fluorescently labeled polysaccharide, the borax solution has a concentration of about 0.2 M, the borax solution and the polysaccharide have a ratio of (0.1-1):1 (mL:mg).

The present application further provides use of a fluorescently labeled polysaccharide for the preparation of a fluorescent probe.

The above technical solutions of the present application have the following advantages.

1. A fluorescently labeled polysaccharide provided by the present application, which is formed by covalently coupling a polysaccharide to a fluorescent dye having a structure represented by formula I. The fluorescently labeled polysaccharide has advantages of high stability in detection environments such as serum, and high biocompatibility and low toxicity, and may be widely applied to polysaccharide detection inside and outside cells, in tissues and living animals, which is of great significance in the fields of polysaccharide absorption, metabolic excretion detection and pharmacological research.

Since the fluorescent dye represented by formula I has a large Stokes shift, the emission wavelength and the excitation wavelength of the fluorescent dye molecule are further separated from each other, so that the fluorescently labeled polysaccharide has advantages of a good fluorescence stability, a high fluorescence quantum yield and a high signal-to-noise ratio of imaging results when used for fluorescence detection. In addition, the long Stokes position is advantageous for increasing the discrimination among different fluorescent dye molecules, and is suitable for multiple fluorescence detection, thereby facilitating the detection of a plurality of types of polysaccharide molecules labeled by different fluorescence. Moreover, the fluorescently labeled polysaccharide provided by the present application is suitable for use as a liquid phase chip probe for detecting the saccharide molecules inside and outside organisms, and increases the detection objects of the liquid phase chip and the types of fluorescently labeled probe.

2. The method of preparing the fluorescently labeled polysaccharide provided by the present application has the advantages that the raw materials required for the reaction are easy to obtain, the reaction conditions are mild, the operation is simple, the selectivity of the reaction is high, and the resultant fluorescently labeled polysaccharide has a high fluorescence yield, a high fluorescence stability and a high biological activity.

DESCRIPTION OF THE DRAWING

In order to more clearly illustrate the technical solutions of the embodiments of the present application or the prior art, the drawings used in the embodiments of the present application or the prior art will be briefly described below. Obviously, the drawings in the following description only represent some embodiments of the present application, and those skilled in the art can obtain other drawings based on these drawings without any creative efforts.

DETAILED DESCRIPTION

Figure 1:
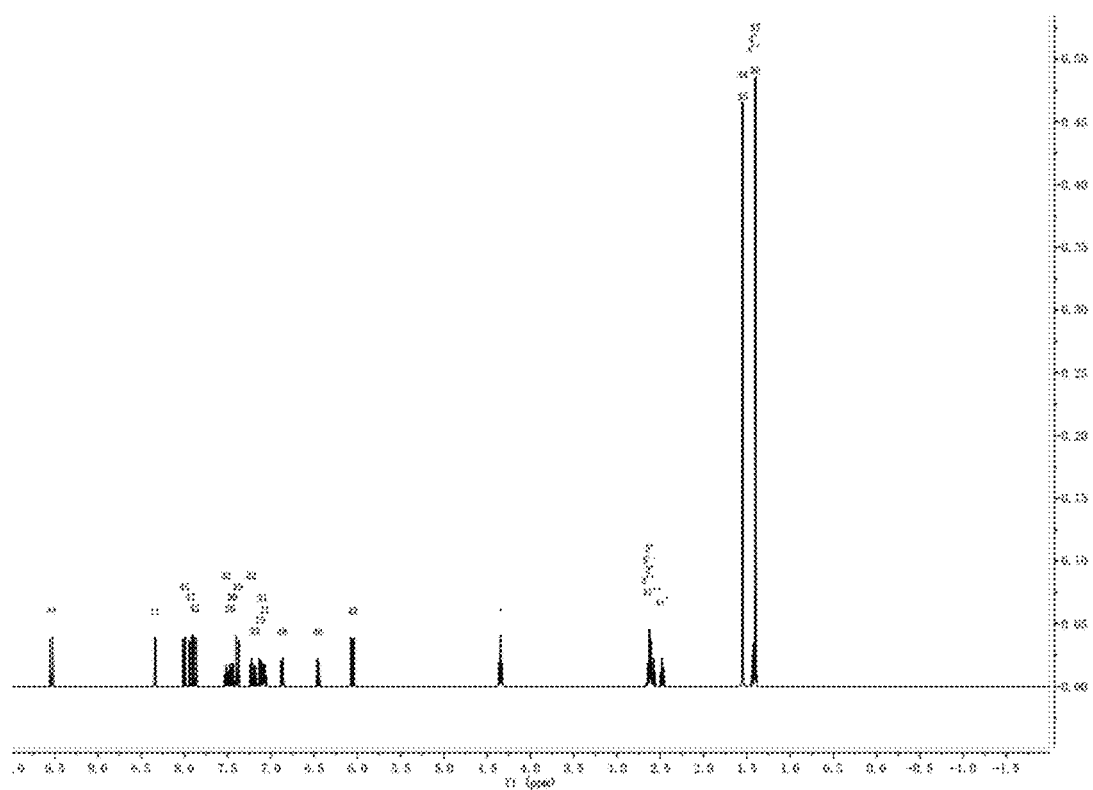
FIG. 1 is a 1H nuclear magnetic spectrum of compound B in Example 1.

The technical solutions of the present application will be described clearly and completely with reference to the accompanying drawings. It is obvious that the described embodiments are only a part of the embodiments of the present application, and not all of the embodiments. All other embodiments obtained by those skilled in the art based on the embodiments of the present application without any creative efforts are within the scope of the present application. Further, the technical features involved in the different embodiments of the present application described below may be combined with each other as long as a conflict is constituted.

The basic chemical raw materials such as reagents used in the embodiments of the present application can be purchased in the domestic chemical product market, or can be customized in the relevant intermediate preparation factory.

Nuclear magnetic resonance apparatus (Bruker DRX-500), High performance liquid chromatography (Waters 2445), Gamma counter (Perkin-Elmer 1470), Elemental analyzer (Perkin-Elmer 240C), Enzyme-linked immunosorbent assay (Bio-Rad, USA) High-speed centrifuge (Beckman Coulter J2-HS). All of the cells involved in the following examples were purchased from the Institute of Cell Research, Shanghai Institutes for Biological Sciences.

Example 1

Example 1 provided a fluorescent dye having a structure represented by the following formula B.

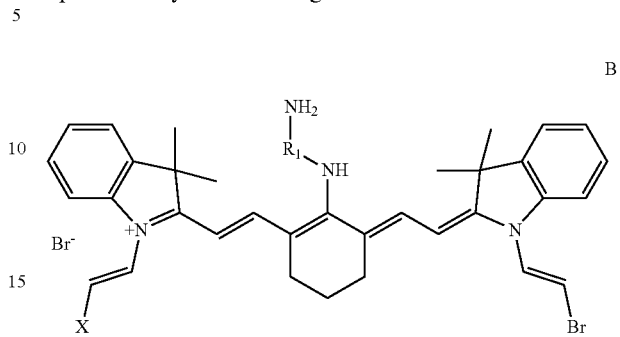

Elemental Analysis Calculated Value: $C_{35}H_{39}Br_3N_4$

Mass Spectrum (MS+): 752.07 (M+) m/z: 754.07 (100.0%), 756.07 (97.7%), 755.07 (39.3%), 757.07 (38.7%), 752.07 (34.2%), 758.07 (32.0%), 753.08 (13.1%), 759.07 (12.2%), 756.08 (7.1%), 758.08 (7.0%), 754.08 (2.4%), 760.07 (2.4%).

Elemental analysis: C, 55.65; H, 5.20; Br, 31.73; N, 7.42.

Example 2

Example 2 provided a fluorescently labeled polysaccharide, wherein the polysaccharide was glucan (purchased from sigma, article number 00268), and the molecular structure of the fluorescent dye was as follows:

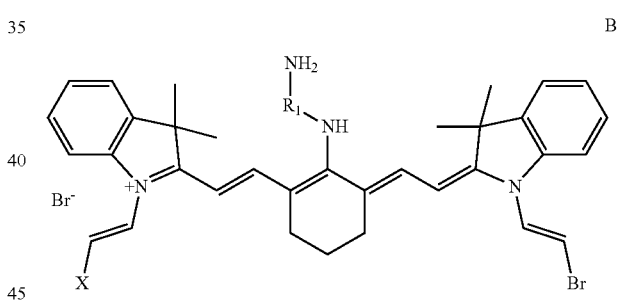

The method of preparing the fluorescently labeled polysaccharide included the following steps of:
1. a saturated cyanogen bromide solution and 0.2M NaOH solution were prepared;
2. 20 mg glucan was weighed, and then dissolved in 1ml distilled water, stirred to ensure full dispersion; 4 ml cyanide bromide solution was added, 250 NaOH solution was added each time, continuously adding for 7 min (ensuring pH>10) to obtain a reaction solution. Observing the changes of the reaction solution, if a precipitation occurred in the reaction solution, the experiment failed and needed to be redone;
3. the reaction solution obtained in the above step 2 was dialyzed against distilled water for 1-2 days, and the dialysate outside the bag was exchanged every 2-3 hours; the solution inside the bag was concentrated to dry to obtain a concentrate, and 5-10 ml of 0.2 M $Na_2B_4O_7 \cdot 12H_2O$ (borax) with pH=8 was added for dissolving the concentrate, and a small amount of a fluorescent dye (about 1.5 mg) represented by formula A was added to react overnight in the dark to obtain a reaction solution, which was transferred to a water bath of 40° C. to continue the reaction in the dark for 24 h. After the reaction was stopped, centrifuging to obtain a supernatant which was dialyzed against distilled water in the dark for two days, followed by centrifugation and lyophilization to obtain a fluorescently labeled glucan. A schematic diagram of a method for labeling polysaccharides with fluorescent dyes was as follows:

A was added to react overnight in the dark to obtain a reaction solution, which was transferred to a water bath of 40° C. to continue the reaction in the dark for 24 h. After the reaction was stopped, centrifuging to obtain a supernatant, which was dialyzed against distilled water in the dark for two days, followed by centrifugation and lyophilization to obtain a fluorescently labeled chitosan.

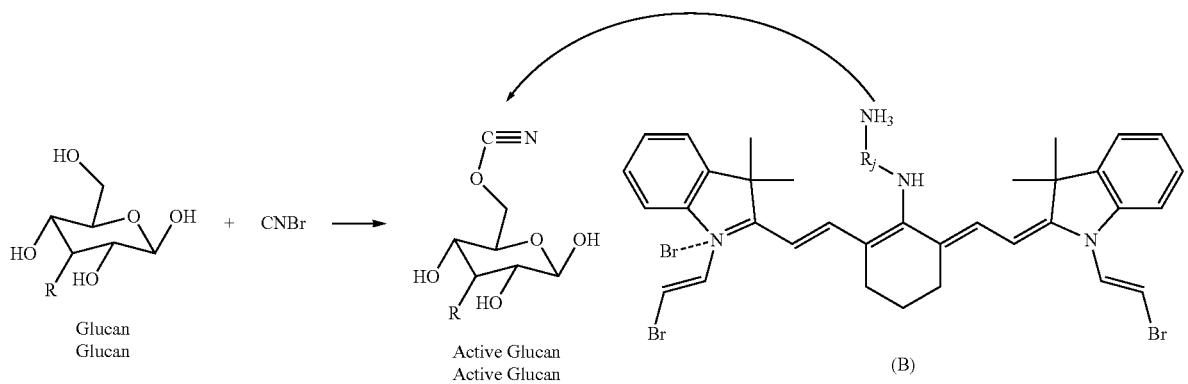

Example 3

Example 3 provided a fluorescently labeled polysaccharide, wherein the polysaccharide was chitosan (purchased from sigma, article number 448869), and the molecular structure of the fluorescent dye was as follows:

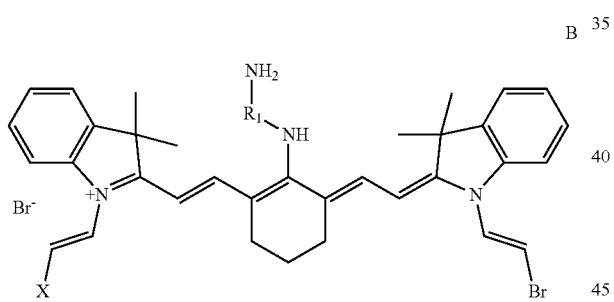

The method of preparing the fluorescently labeled polysaccharide included the following steps of:

1. a saturated cyanogen bromide solution and 0.2M NaOH solution were prepared;
2. 10 mg chitosan was weighed, and then dissolved in 1 ml distilled water, stirred to ensure full dispersion; 4 ml cyanide bromide solution was added, 250 NaOH solution was added each time, continuously adding for 9 min (ensuring pH>10) to obtain a reaction solution. Observing the changes of the reaction solution, if a precipitation occurred in the reaction solution, the experiment failed and needed to be redone.
3. the reaction solution obtained in the above step 2 was dialyzed against distilled water for 1-2 days, and the dialysate outside the bag was exchanged every 2-3 hours; the solution inside the bag was concentrated to dry to obtain a concentrate, and 1-10 ml of 0.2 M $Na_2B_4O_7 \cdot 12H_2O$ (borax) with pH=8 was added for dissolving the concentrate, and a small amount of a fluorescent dye (about 1.5 mg) represented by formula Experimental Example 1 Fluorescence Property Detection of the Fluorescent Dyes 1. The compound B to be measured was accurately weighed to prepare a solution having a concentration of $1.0 \times 10^{-5}$ mol/L using 50% by volume of ethanol. The fluorescence spectrum of the solution was measured to obtain a maximum absorption wavelength (2\, a b s) in the near-infrared spectrum of the compound.
2. The fluorescence spectrum was measured using the maximum absorption wavelength in the measured near-infrared spectrum as the excitation wavelength of the fluorescence spectrum. The compound to be measured was accurately weighed to prepare a solution of ethanol and water (50:50, v/v) at a concentration of $1.0 \times 10^{-6}$ mol/L. The emission wavelength (A em) of the emission spectrum of the solution was measured to calculate the Stokes shift as shown in Table 1.
3. Measurement of Molar Extinction Coefficient of Fluorescent Dyes The molar extinction coefficient of the compound was measured by UV-visible absorption spectroscopy. The formula for calculating molar extinction coefficient is as shown in equation (1):

$$A = \varepsilon c l \quad \text{Equation (1)},$$

wherein A represents ultraviolet absorption value, ε represents molar extinction coefficient, c represents concentration of the compound, and l represents thickness of the quartz cell for detection.

4. Measurement of Fluorescence Quantum Yield of Fluorescent Dyes

The fluorescence quantum yield of the fluorescent dyes was determined at 20° C., and quinine sulfate (Solvent: 0.1M $H_2SO_4$, Quantum yield: 0.56) was used as a reference compound, then the fluorescence quantum yield was calculated by measuring fluorescence integral intensities obtained from the dilute solutions of the fluorescent dyes and the reference compound under the same excitation conditions and the ultraviolet absorption value at this excitation wavelength. The product was dissolved in absolute ethanol.

The formula for calculating fluorescence quantum yield is as shown in equation (2):

$$\Phi = \Phi_R \times \frac{I}{I_R} \times \frac{A_R}{A} \times \frac{\eta^2}{\eta_R^2},\qquad \text{Equation (2)}$$

wherein Φ represents quantum yield of the compound to be measured, the subscript R represents reference compound, I represents fluorescence integral intensity, A represents ultraviolet absorption value, and η represents solvent refractive index. Generally, the ultraviolet absorption values A and $A_R$ are less than 0.1.

TABLE 1

Spectroscopic properties of the fluorescent dyes of example 1

| | $\lambda_{abs}$ (mlx/nm) | $\lambda_{em}$ (mlx/nm) | $\varepsilon \times 10^4$ ($M^{-1}cm^{-1}$) | Φ (%) | Stokes shift (nm) |
|---|---|---|---|---|---|
| Compound represented by the formula B | 786 | 821 | 8.6 | 85.06 | 40 |

As shown in Table 1, the fluorescent dye represented by formula B has a fluorescence quantum yield of >85% and a large Stokes shift, and is suitable for preparing a fluorescent probe by labeling biomolecules such as polysaccharides, and achieves detection of a nucleic acid molecule having advantages of stable fluorescence performance, high fluorescence quantum yield, and high imaging signal-to-noise ratio.

Experimental Example 2 Toxicity Detection of Fluorescently Labeled Polysaccharide Cytotoxicity Test The cytotoxicity of the fluorescently labeled glucan prepared in Example 2 and the fluorescently labeled chitosan prepared in Example 3 in HEK-293T (human embryonic kidney cells) was determined by MTT assay, including the following steps:

(1) HEK-293T cells were seeded in a 96-well plate at a density of 5×10³ cells/100 μL per well, using DMEM as the medium, and were cultured overnight at 37° C. in a constant temperature incubator containing 5% $CO_2$.

(2) The fluorescently labeled glucan prepared in Example 2 and the fluorescently labeled chitosan prepared in Example 3 were dissolved in dimethyl sulfoxide (DMSO) to prepare a mother liquor having a concentration of 0.1 mol/L, which was diluted with DMEM medium to solutions having a concentration of 80 μmol/L, 40 μmol/L, 20 μmol/L, 10 μmol/L and 5 μmol/L respectively for reserve. In addition, the DMEM medium was diluted with an equal volume of deionized water, wherein the fluorescently labeled polysaccharide had a concentration of 0 μmol/L.

(3) The original medium in the 96-well plate in the step (1) was replaced with DMEM medium with drug concentrations of 0 μmol/L, 5 μmol/L, 10 μmol/L, 20 μmol/L, 40 μmol/L and 80 μmol/L prepared in the above step (2), 200 μL per well, and 6 replicate wells were set per drug concentration. The 96-well plates were then incubated for 3 h, 6 h, 12 h, and 24 h at 37° C. in a 5% $CO_2$ incubator, respectively. After completing the incubation, 20 μL MTT (5 mg/mL) was added to each well for further culture of 4 h. After completing the culture, the medium was removed, 150 μL DMSO was added to each well, shaking on a shaker for 10 minutes until crystals were completely dissolved. The absorbance value of each well at 490 nm was determined by enzyme labeling, and the experimental results were the average of values of at least three independent experiments.

Figure 2:
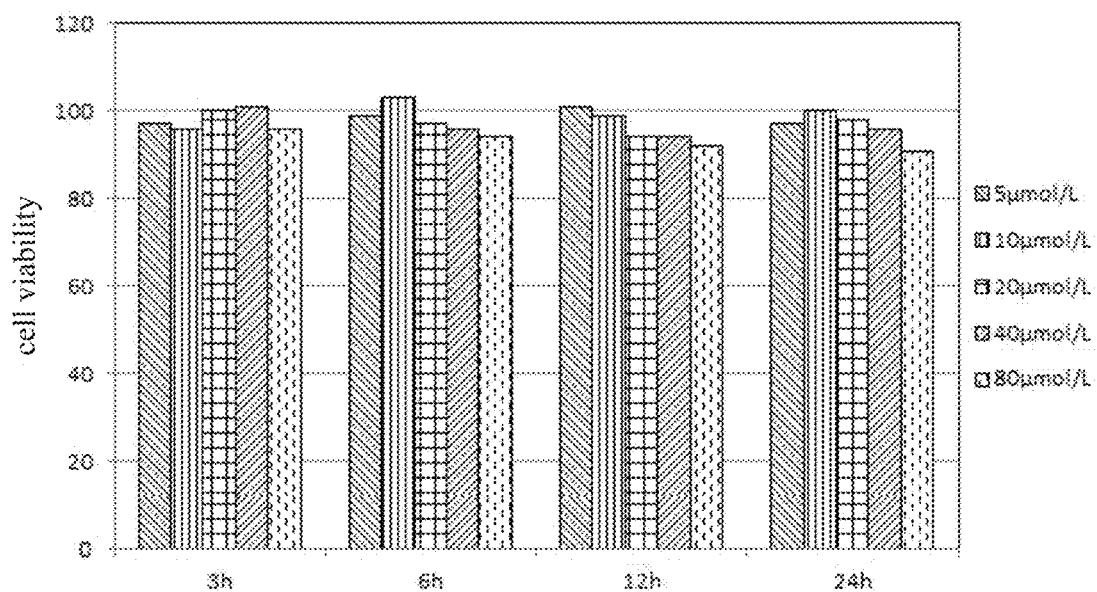
FIG. 2 is a histogram of the influence of fluorescently labeled glucan prepared in Experimental Example 2 of the present application on the cell viability of HEK-293T cells at different concentrations.
Figure 3:
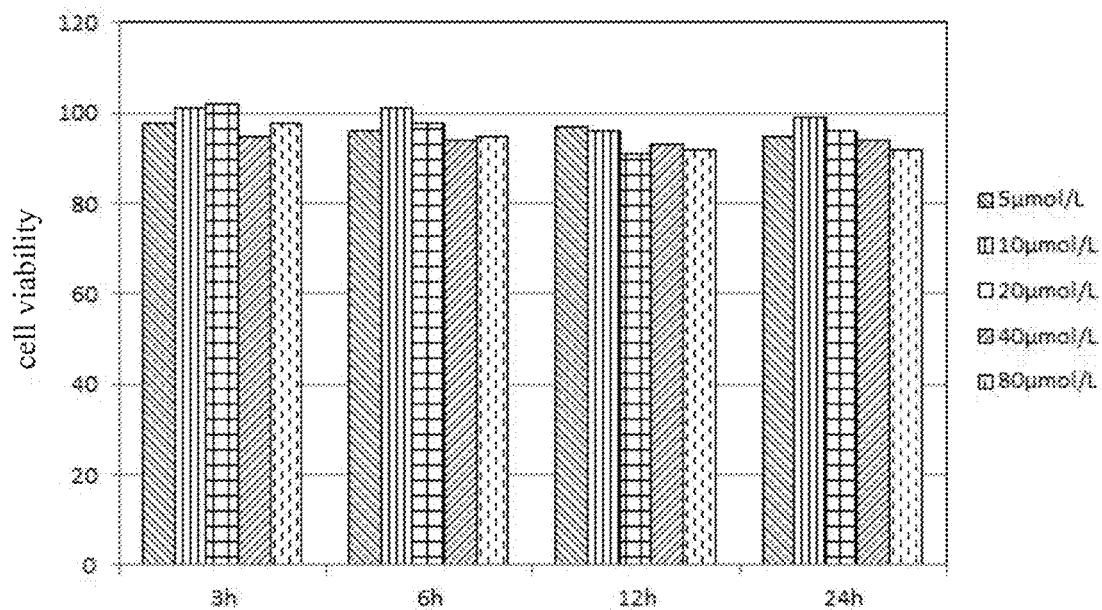
FIG. 3 is a histogram of the influence of fluorescently labeled chitosan prepared in Experimental Example 3 of the present application on cell viability of HEK-293T cells at different concentrations.

A histogram of the influence of fluorescently labeled glucan on the cell survival rate of HEK-293T cells at different drug concentrations and different incubation times is shown in FIG. 2. The influence of fluorescently labeled chitosan on cell survival rate of HEK-293T cells is shown in FIG. 3. The change of cell survival rate is not significant with the prolongation of drug action and the increase of compound concentration, and the cell survival rate is greater than 90% within 24 h, so it can be determined that the fluorescently labeled polysaccharide is safe and low toxic to HEK-293T cells, and has good biocompatibility.

Figure 4:
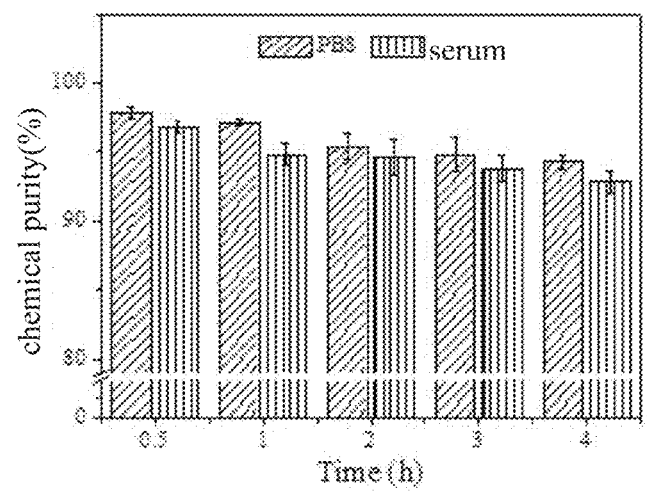
FIG. 4 is a graph showing the chemical purity of fluorescently labeled glucan prepared in Experimental Example 2 of the present application incubated in PBS or serum for different times.

Experimental Example 3 Stability Test of Fluorescently Labeled Polysaccharide (1) 4 parts of 800 μL PBS (pH=7.4) buffer and 200 μL of the fluorescently labeled glucan solution prepared in Example 2 were separately mixed and heated at 37° C. for 0.5 h, 1 h, 2 h, 3 h, 4 h. Small amount of the above solutions were diluted, and the stability of the labeled products was detected by radioactive high-performance liquid phase. The conditions of High-performance liquid phase were that: water (containing 0.1% by volume of TFA) was used as mobile phase A, and $CH_3CN$ (containing 0.1% by volume of TFA) was used as mobile phase B, the gradient elution was performed according to the following procedures: 0 min→3 min, the volume ratio of mobile phase A to mobile phase B was 80:20→80:20; 3 min→25 min, the volume ratio of mobile phase A to mobile phase B was 80:20→10:90; 25 min→30 min, the volume ratio of mobile phase A to mobile phase B was 10:90→80:20; and the flow rate of the mobile phase was controlled to 1 mL/min, the temperature of a column was controlled at 25° C. Then, 4 parts of 800 μL mouse serum (purchased from Biyuntian) and 200 μL of the solution of the fluorescently labeled glucan prepared in Example 2 were separately mixed and heated at 37° C. for 0.5 h, 1 h, 2 h, 3 h, 4 h. 100 μL the above solution was added to 100 μL acetonitrile, centrifuging at 10,000 g for 5 min in a high-speed centrifuge to obtain a supernatant, the stability of the labeled product of the supernatant was detected by high performance liquid chromatography. The conditions of High-performance liquid phase were that: water (containing 0.1% by volume of TFA) was used as mobile phase A, and CH 3 CN (containing a volume concentration of 0.1% of TFA) was used as mobile phase B, and the gradient elution was performed according to the following procedures: 0 min→3 min, the volume ratio of mobile phase A to mobile phase B was 80:20→80:20; 3 min→25 min, the volume ratio of mobile phase A to mobile phase B was 80:20→10:90; 25 min→30 min, the volume ratio of mobile phase A to mobile phase B was 10:90→80:20, the flow rate of the mobile phase was controlled to 1 mL/min, and the temperature of a column was controlled at 25° C. FIG. 4 was a graph showing the chemical purity of fluorescently labeled glucan incubated in PBS or serum for different times.

Figure 5:
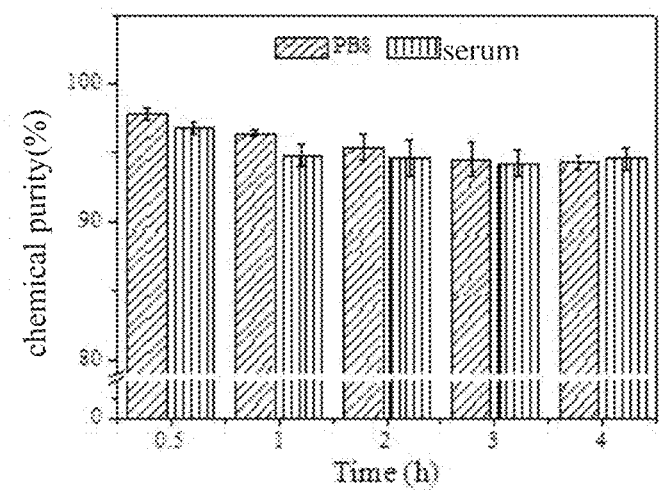
FIG. 5 is a graph showing the chemical purity of fluorescently labeled chitosan prepared in Experimental Example 3 of the present application incubated in PBS or serum for different times.

(2) The chemical purity of the fluorescently labeled chitosan after incubation in PBS or serum for different times was measured by the detection method in the step (1), and the results were shown in FIG. 5.

It can be seen from FIGS. 4 and 5 that, the radiochemical purities of fluorescently labeled chitosan and fluorescently labeled glucan in PBS and serum decrease slightly with the increase of incubation time, and the chemical purities in PBS and serum are still greater than 95% at 4 h, indicating that the fluorescently labeled amino acid has a good stability in vitro and is advantageous for further in vivo experimental studies.

Experimental Example 4 Fluorescence Intensity Detection of Fluorescently Labeled Polysaccharide (1) HEK-293T cells were cultured to a logarithmic phase in an incubator with 5% $CO_2$ at 37° C.;
(2) The cultured cells were seeded at $1\times10^5$ cells/well in a 12-well plate containing slides (the slides were immersed in 75% ethanol for 5 min to disinfect, and purchased from Assitent), and cultured overnight.
(3) The cell supernatant was removed, and the fluorescently labeled glucan prepared in Example 2 and the fluorescently labeled chitosan prepared in Example 3, which were diluted with the medium, at a final concentration of 1 mg/ml, were separately added, and then placed in a cell culture incubator for further culture for 24 h.
(4) After termination of the culture, the slide in the well plate was moved to a new 12-well plate, PBST (containing 0.1% Tween-20) was added for rinse 3-4 times. 4% paraformaldehyde was added for fixation for 15 min at room temperature, PBST was added for rinse 3-4 times. DAPI (purchased from Cell Signal, USA) solution with a final concentration of 1 μg/ml was added for incubation for 15 min at 37° C., PBST was added for rinse 3-4 times. Mounting, and observation under a laser confocal microscope (purchased from Olympus, Japan) were performed.

Figure 6:
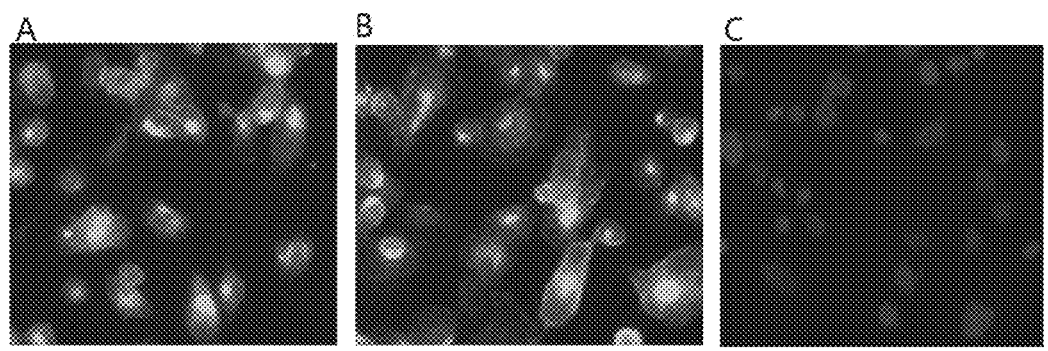
FIG. 6 is a graph showing the detection results of fluorescence intensity of fluorescently labeled polysaccharides in HEK-293T cells.

FIG. 6 shows the results of fluorescence intensity detection of fluorescently labeled polysaccharides in HEK-293T cells, wherein figures from left to right represent the fluorescence detection results of fluorescently labeled glucan in HEK-293T cells, the fluorescence detection results of fluorescently labeled chitosan in HEK-293T cells, and DAPI staining results of HEK-293T cells, respectively. It can be seen from FIG. 6 that a significant fluorescence intensity is detected in cells incubated with fluorescently labeled glucan and fluorescently labeled chitosan, indicating that HEK-293T cells can uptake the above-mentioned fluorescently labeled polysaccharide, and the polysaccharide has a high fluorescence intensity after being labeled with a fluorescent dye.

It is apparent that the above embodiments are merely examples for clarity of illustration, and are not intended to limit the embodiments. Other variations or modifications of the various forms may be made by those skilled in the art in view of the above description. There is no need and no way to present all of the embodiments herein. The obvious variations or modifications derived therefrom are still within the scope of protection of the present application.

The invention claimed is:

1. A fluorescently labeled polysaccharide, wherein the fluorescently labeled polysaccharide is formed by covalently coupling a polysaccharide to a fluorescent dye having a structure represented by the formula (I):

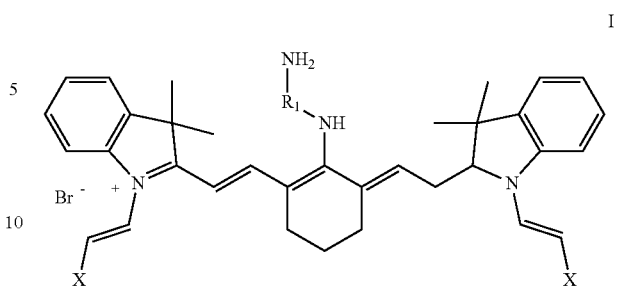

wherein X is halogen; $R_1$ is selected from one of hydrogen, [alkylene], cycloalkyl, aryl and heterocyclyl.

2. The fluorescently labeled polysaccharide according to claim 1, wherein the polysaccharide is activated by cyanogen bromide, and the polysaccharide is covalently coupled to the dye through a cyano group, wherein the cyano group binds to a hydroxyl group of the polysaccharide and to the amino group of the dye.

3. The fluorescently labeled polysaccharide according to claim 2, wherein X is Br.

4. The fluorescently labeled polysaccharide according to claim 3, wherein the fluorescent dye has a structure represented by formulas [B] to G:

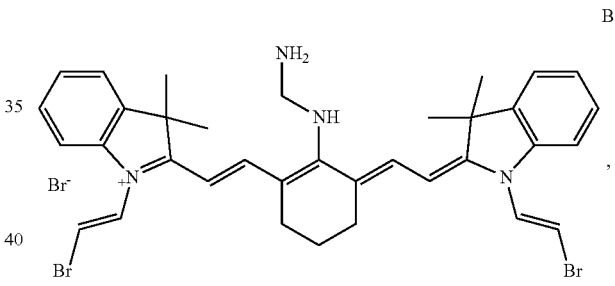

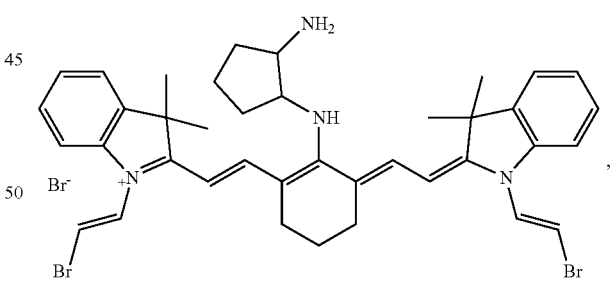

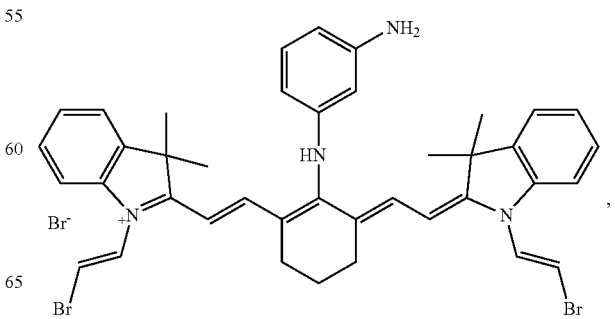

E

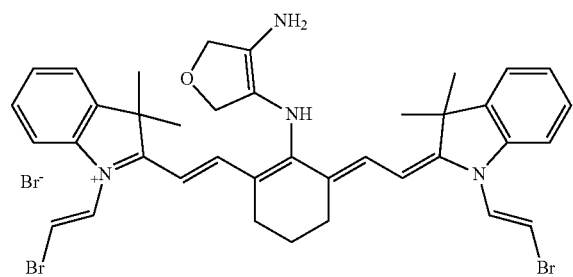
,

F

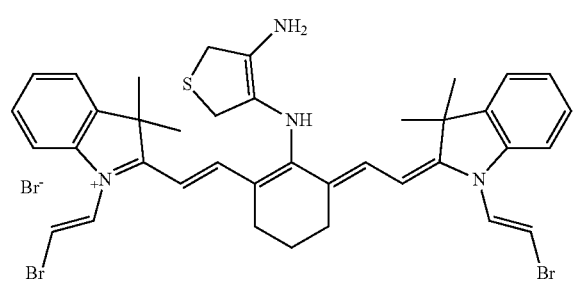
,

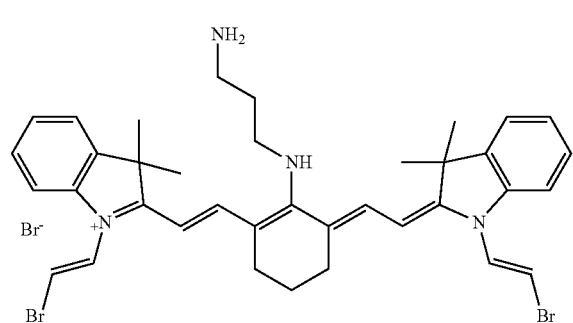
.

5. The fluorescently labeled polysaccharide according to claim 2, wherein the fluorescent dye has a structure represented by formulas [B] to G:

B

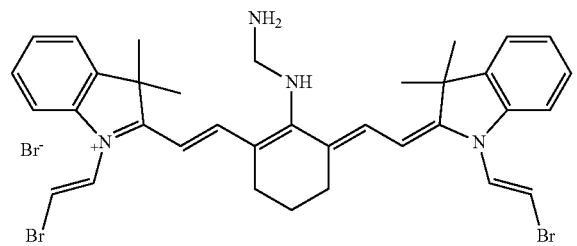
,

C

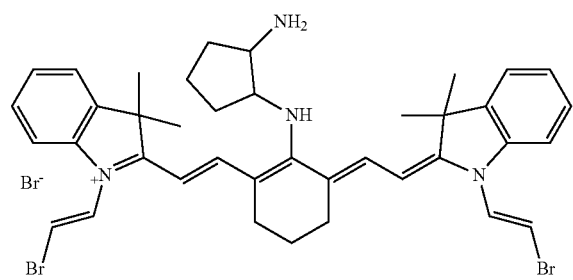
,

D

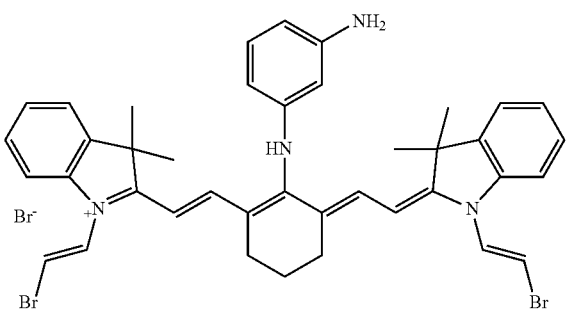
,

E

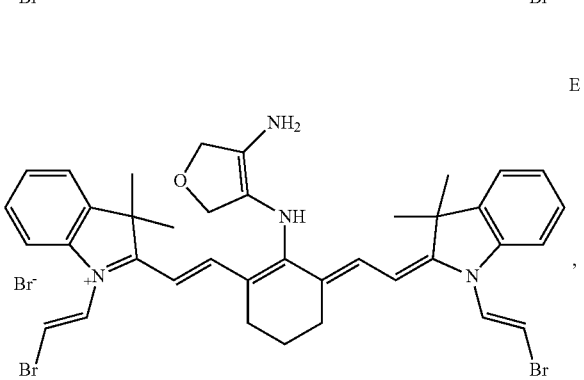
,

F

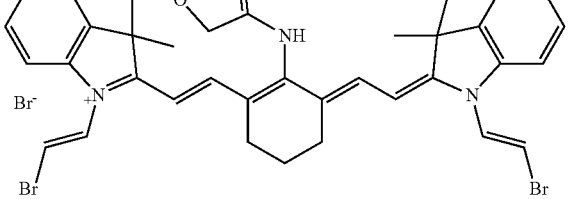
,

G

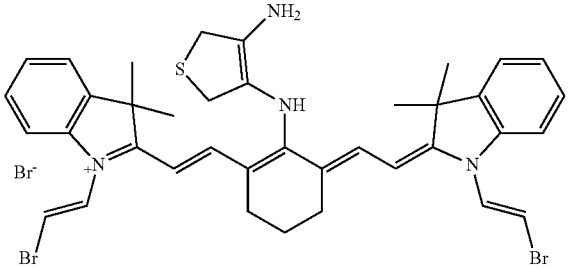
.

6. The fluorescently labeled polysaccharide according to claim 2, wherein the polysaccharide is selected from at least one of glucan, chitosan, pectic polysaccharide, grifola frondosa polysaccharide, ganoderan, lentinan and spirulina polysaccharide.

7. The fluorescently labeled polysaccharide according to claim 1, wherein X is Br.

8. The fluorescently labeled polysaccharide according to claim 7, wherein the fluorescent dye has a structure represented by formulas [B] to G:

B
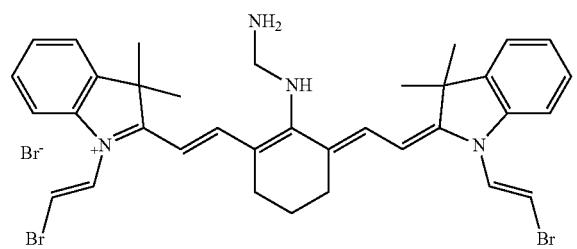,

C
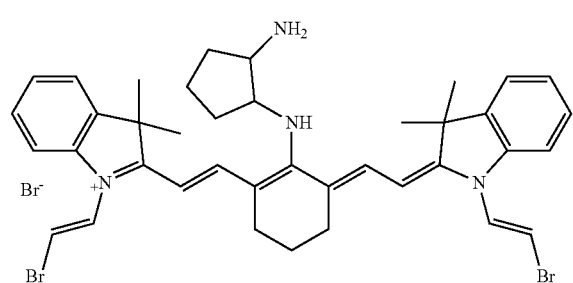,

D
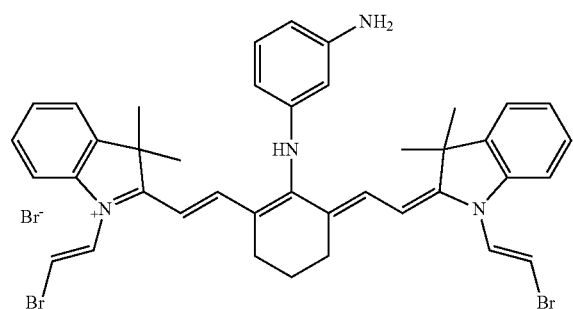,

E
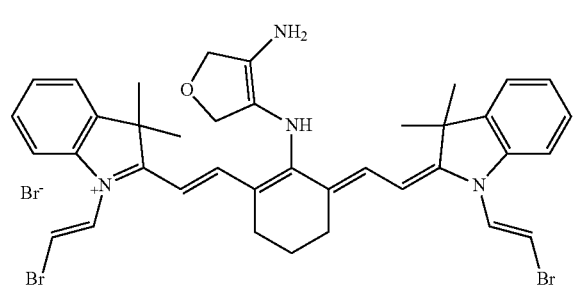,

F
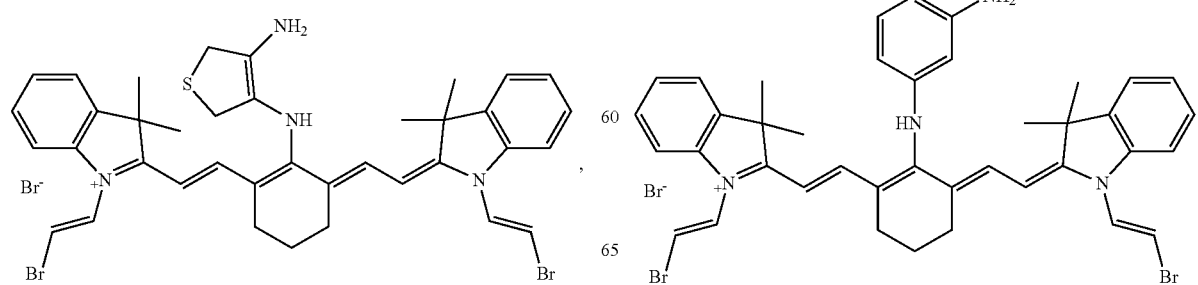,

G
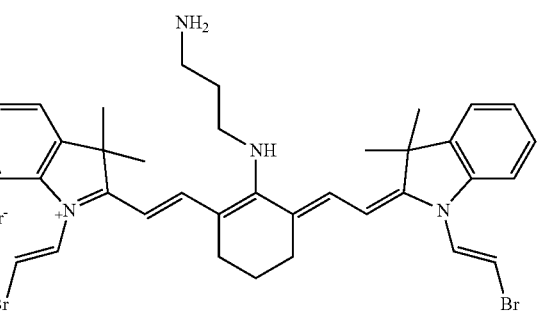.

9. The fluorescently labeled polysaccharide according to claim 7, wherein the polysaccharide is selected from at least one of glucan, chitosan, pectic polysaccharide, grifola frondosa polysaccharide, ganoderan, lentinan and sprulina polysaccharide.

10. The fluorescently labeled polysaccharide according to claim 1, wherein the fluorescent dye has a structure represented by formulas [B] to G:

B
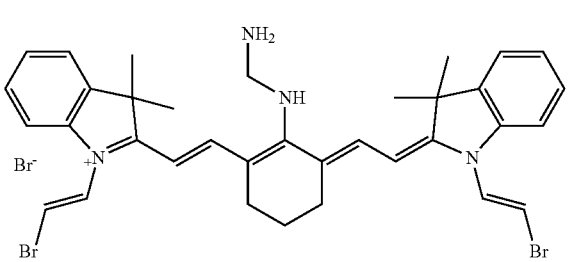,

C

D

-continued

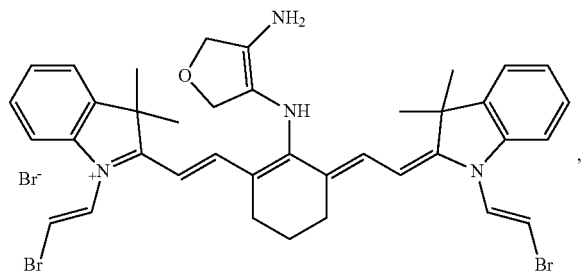

E

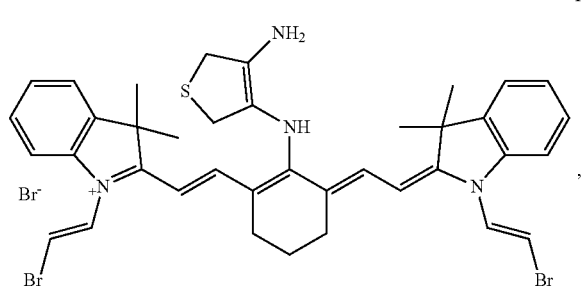

F

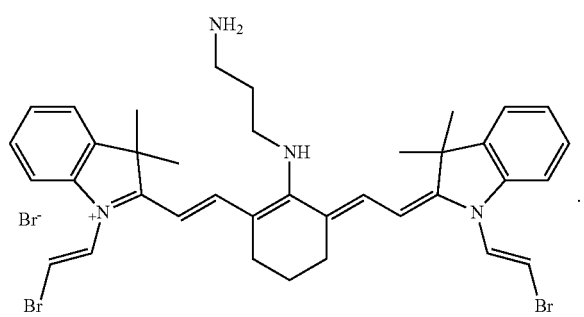

G

11. The fluorescently labeled polysaccharide according to claim 10, wherein the polysaccharide is selected from at least one of glucan, chitosan, pectic polysaccharide, grifola frondosa polysaccharide, ganoderan, lentinan and spriulina polysaccharide.

12. The fluorescently labeled polysaccharide according to claim 1, wherein the polysaccharide is selected from at least one of glucan, chitosan, pectic polysaccharide, grifola frondosa polysaccharide, ganoderan, lentinan and spriulina polysaccharide.

13. A method of preparing the fluorescently labeled polysaccharide according to claim 1, comprising the steps of:
   (1) dissolving the polysaccharide in water, and then adding a saturated cyanogen bromide solution for reaction for 3-20 minutes, and purifying the solution obtained after the reaction;
   (2) concentrating the purified solution obtained in the step (1) to dry, dissolving in 0.1-0.3 M borax solution, and then adding a fluorescent dye represented by the formula I for reaction in the dark to obtain the fluorescently labeled polysaccharide.

14. The method according to claim 13, wherein in the step (1), the reaction is carried out under the condition of pH>10; and/or, the reaction time is controlled for 5-10 minutes.

15. The method according to claim 14, wherein in the step (2), the borax solution has a concentration of about 0.2 M, the borax solution and the polysaccharide have a ratio of (0.1-1):1 (mL:mg).

16. The method according to claim 13, wherein in the step (2), the borax solution has a concentration of about 0.2 M, the borax solution and the polysaccharide have a ratio of (0.1-1):1 (mL:mg).

17. A method of preparing a fluorescent probe, comprising the step of using a fluorescently labeled polysaccharide according to claim 1.

* * * * *